United States Patent [19]

Partyka et al.

[11] 4,315,023
[45] Feb. 9, 1982

[54] 1-PHENETHYLIMIDAZOLE DERIVATIVES

[75] Inventors: Richard A. Partyka, Liverpool, N.Y.;
Thomas W. Hudyma, Manlius, N.Y.

[73] Assignee: Westwood Pharmaceuticals, Inc., Buffalo, N.Y.

[21] Appl. No.: 211,986

[22] Filed: Dec. 1, 1980

Related U.S. Application Data

[63] Continuation-in-part of Ser. No. 73,041, Sep. 6, 1979, abandoned.

[51] Int. Cl.$^3$ .................. A61K 31/415; C07D 233/60
[52] U.S. Cl. .......................... 424/273 R; 548/336; 548/341
[58] Field of Search .................. 548/336, 341; 424/273 R

[56] References Cited

U.S. PATENT DOCUMENTS 4,177,530 12/1979 Zvingibl et al. ............. 548/341 X

Primary Examiner—Richard Raymond
Attorney, Agent, or Firm—Morton S. Simon

[57] ABSTRACT

1-Phenethylimidazole compounds of the formula:

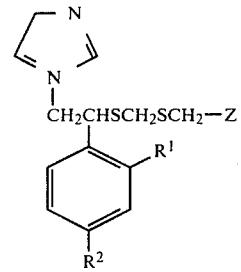

wherein $R^1$ and $R^2$ are independently hydrogen or halogen, Z is a mono or disubstituted phenyl moiety of the formula:

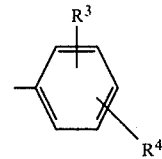

or a 2 or 3-thienyl moiety of formula:

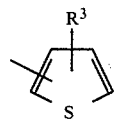

wherein $R^3$ and $R^4$ are independently hydrogen, halogen, (lower) alkyl, or trifluoromethyl, with the proviso that $R^3$ and $R^4$ can not both be trifluoromethyl and the antimicrobial acid addition salts thereof are useful as antifungal and antibacterial agents.

43 Claims, No Drawings

1-PHENETHYLIMIDAZOLE DERIVATIVES

This application is a continuation-in-part of copending application Ser. No. 73,041 filed Sept. 6, 1979, now abandoned.

DESCRIPTION

This invention relates to certain novel 1-phenethylimidazole derivatives and their antimicrobial acid addition salts, antimicrobial compositions containing the same, and methods of employing such derivatives, salts and compositions for inhibiting the growth of fungi and bacteria.

PRIOR ART

A large number of antifungal and antibacterial agents have been previously described which contain a 1-(β-aryl)ethyl-1H-imidazole moiety of the formula:

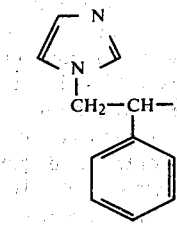

For example, in U.S. Pat. No. 3,717,655 and E. F. Godefroi et al, J. Med. Chem. 12, 784 (1969), compounds of formula 1 are disclosed in which $R_a$ is:

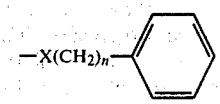

wherein X is O or NH.

In U.S. Pat. No. 3,991,201 and J. Heeres et al, J. Med. Chem. 20, 1511 (1977), such compounds are disclosed in which $R_a$ is $-(CH_2)_n-Ar$.

In J. Heeres et al, J. Med. Chem. 20, 1516 (1977), such compounds are disclosed in which $R_a$ is $-(CH_2)_nO-Ar$.

In U.S. Pat. Nos. 4,055,652 and 4,039,677, such compounds are disclosed in which $R_a$ is $-SR_2$ wherein $R_2$ is H, benzyl, phenyl, etc.

In U.S. Pat. Nos. 4,039,677 and 4,038,409, such compounds are disclosed in which $R_a$ is

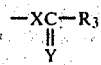

wherein X and Y are O or S and $R_3$ is H, alkyl, cycloalkyl, phenalkyl, phenalkenyl, or $-XR_4$ wherein $R_4$ is alkyl, halophenyl, etc.

In U.S. Pat. No. 4,006,243, such compounds are disclosed in which $R_a$ is H, alkyl or phenyl.

In U.S. Pat. No. 4,177,350, such compounds are claimed in which $R_a$ is a group of the formula:

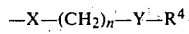

wherein $R^4$ is hydrogen, lower alkyl or an unsubstituted or substituted cycloalkyl, benzyl, phenyl or pyridyl group, X and Y are independently selected from oxygen (—O—) or sulfur (—S—) and n is an integer of from 1 to 5 inclusive. In U.S. Pat. No. 4,177,350 $R_a$ therefore encompasses the following four side chains:

$R_a^1 = -O-(CH_2)_n-O-R^4$
$R_a^2 = -O-(CH_2)_n-S-R^4$
$R_a^3 = -S-(CH_2)_n-O-R^4$
$R_a^4 = -S-(CH_2)_n-S-R^4$ wherein $R^4$ and n are as defined above. In the preferred embodiments of U.S. Pat. No. 4,177,350 it is defined that in side chain $R_a^4$, n is preferably 2 and $R^4$ is 4-chlorophenyl. The preparation of this preferred compound 2 is described in

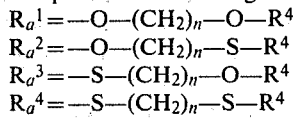

Example 21 of U.S. Pat. No. 4,177,350. The preparation and biological activities of compounds in whose side chain $R_a^4$ n=1 and $R^4$=substituted benzyl or thienyl are not described in U.S. Pat. No. 4,177,350. In fact there is no teaching or even suggestion in U.S. Pat. No. 4,177,350 that would lead one skilled in the art to expect that compounds with side chain $R_a^4$ wherein n=1 and $R^4$=substituted benzyl or thienyl would represent an important advance in antimycotic therapy.

DESCRIPTION OF THE PRESENT INVENTION

This invention relates to novel antimicrobial 1-phenethylimidazole compounds of the general formula 3,

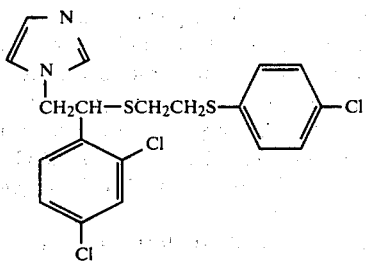

wherein $R^1$ and $R^2$ are independently hydrogen or halogen and Z is a mono or disubstituted phenyl moiety of formula 4 or a 2 or 3 thienyl moiety of formula 5,

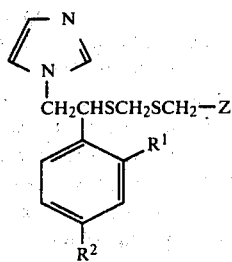

wherein $R^3$ and $R^4$ are independently selected from the group consisting of hydrogen, halogen, (lower) alkyl and trifluoromethyl, with the proviso that only one of the $R^3$, $R^4$ substituents may be trifluoromethyl. This invention also relates to the antimicrobial (i.e. antifungal, antibacterial) acid addition salts of the compounds of the formula 3.

As used herein and in the claims: The term "(lower) alkyl" means an alkyl group, either straight or branched chain, containing from one to three carbon atoms. "Halogen" or "halo" refers to chloro, bromo and fluoro, preferably chloro. The term "antimicrobial acid addition salts" refers to the crystalline salts of the subject compounds which possess the desired antimicrobial activity and which are neither biologically nor otherwise undesirable. Such salts are formed by contacting the subject compounds with inorganic acids such as hydrochloric, hydrobromic, hydroiodic, nitric, sulfuric and phosphoric acids, and organic acids such as fumaric, oxalic, maleic, acetic, pyruvic, citric, tartaric, methanesulfonic, ethanesulfonic, p-toluenesulfonic, hydroxyethanesulfonic, sulfamic, malic, succinic, ascorbic, levulinic, propionic, glycolic, benzoic, mandelic, salicylic, lactic, p-aminosalicylic, 2-phenoxybenzoic, 2-acetoxybenzoic, 1,4-naphthalene disulfonic acids and the like.

The subject compounds of formula 3 are organic bases, the majority of which are viscous oils in the free base form. The free bases are usually purified by column chromatography on either silicic acid or alumina and may then be converted to their solid acid addition salts by contacting them with one of the above salt-forming acids, usually in a solvent such as water, ethanol, 1-propanol, ethyl acetate, acetonitrile or diethyl ether. Upon cooling or dilution with a less polar solvent the acid addition salts usually crystallize.

Such compounds of formula 3 contain a chiral or asymmetric center, i.e. the carbon atom in the depicted CH link, and therefore may exist as enantiomers which may if desired be separated by known procedures such as by conventional resolution means employing optically active acids such as the optically active forms of camphor-10-sulfonic, α-bromocamphor-π-sulfonic, camphoric, menthoxyacetic, tartaric, malic, diacetyltartaric, pyrrolidone-5-carboxylic acids and the like. It will be understood that this invention is inclusive of such optical isomers and the racemic mixtures thereof.

The products of the present invention are named as derivatives of 1-(ethyl)-1H-imidazole with the arylmethylthiomethylthio substituent located on the 2-position (or β-position) of the ethyl side chain.

The subject compounds 3 possess potent in vitro antifungal activity against human and animal pathogenic fungi comparable to that of the closest prior art compound, 2, disclosed in U.S. Pat. No. 4,177,350. It was therefore surprising to discover that, with the exception of the compound of formula 3e, the compounds of the present invention were from about greater than 5 to greater than 270 times more efficacious than prior art compound 2 in the treatment of Candida induced vaginal infection in mice. For example the hydrogen fumarate salt of one of the particularly preferred compounds of formula 3, namely 3a, was found to be greater than 85 times more efficacious than the hydrogen fumarate salt of prior art compound 2 in this in vivo test system and about 2.5 times more efficacious than prior art compound 2 in the treatment of Trichophyton induced skin infection in guinea pigs.

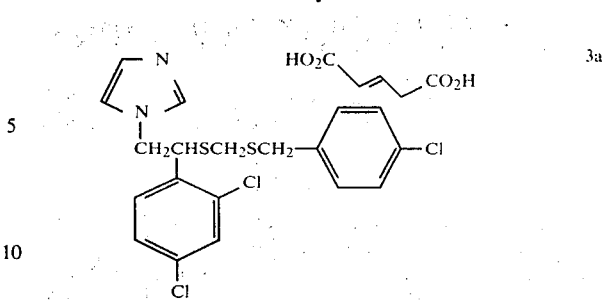

In vivo evaluation of the compounds 3 of the present invention has proven many of same to be unexpectedly superior to the compounds disclosed in U.S. Pat. No. 4,177,350, especially for the treatment of candidiasis (moniliasis), which is a very prevalent fungal infection. For example vaginal candidiasis is common in pregnant women. Candidiasis of the mucous membranes of the buccal cavity is known as thrush and is a common fungal infection in the newborn and children. Thrush can be an especially troublesome infection in newborn infants in hospital nurseries, and with patients who are being treated with steroids or immunosuppressive drugs for other afflictions. Vulvovaginitis is a thrushlike infection that is common in uncontrolled diabetics. The incidence of candidiasis is increasing largely as a result of the prolonged widespread use of potent antibiotic and immunosuppressive drugs. The agents of the present invention represent a valuable contribution to the science of medical mycology for treatment of the aforementioned fungal infections, as well as those infections caused by other fungal pathogens. The compounds of formula 3 also have antibacterial activity, especially against gram positive organisms. The subject compounds of formula 3 above, also exhibit antifungal activity against fungi of primarily agricultural importance. Thus, the subject compounds are found to be useful antimicrobials, having not only pharmaceutical but also agricultural and industrial applications. Thus, a further feature of the present invention relates to methods of inhibiting the growth of fungi and bacteria by applying to a host object containing, or subject to attack by, fungi or bacteria, a fungicidally or bactericidally effective amount of a compound of this invention. A still further feature of the present invention relates to compositions for pharmaceutical, agricultural, and industrial use, which compositions comprise the subject compounds of formula 3 in combination with a suitable carrier.

PREFERRED EMBODIMENTS

Preferred compounds of the present invention are those of formula 3 in which one of the $R^1$ or $R^2$ substituents is chloro and the other is chloro or hydrogen and Z is a mono or disubstituted phenyl moiety of formula 4 or a 2 or 3-thienyl moiety of formula 5, wherein $R^3$ and $R^4$ are independently selected from the group consisting of hydrogen, fluoro, chloro, (lower) alkyl, and trifluoromethyl, with the proviso that only one of the $R^3$, $R^4$ substituents is trifluoromethyl.

In a more preferred embodiment of the compounds of formula 3 at least one of the $R^1$ and $R^2$ substituents is chloro and the other is chloro or hydrogen and Z is a mono or disubstituted phenyl moiety of formula 4 or a 2 or 3-thienyl moiety of formula 5, wherein $R^3$ and $R^4$ are independently selected from the group consisting of hydrogen, chloro and (lower) alkyl.

In a still more preferred embodiment of the compounds of formula 3 R² is chloro and R¹ is hydrogen or chloro and Z is 4-chlorophenyl, 2,4-dichlorophenyl and 2-chloro-3-thienyl.

As presently envisaged, particularly preferred compounds of formula 3 are those in which R¹ and R² are both chloro and Z is 4-chlorophenyl, 4-methylphenyl and 5-chloro-2-thienyl.

PREPARATION OF SUBJECT COMPOUNDS

In a preferred process the compounds of formula 3 are prepared as shown in the following chart.

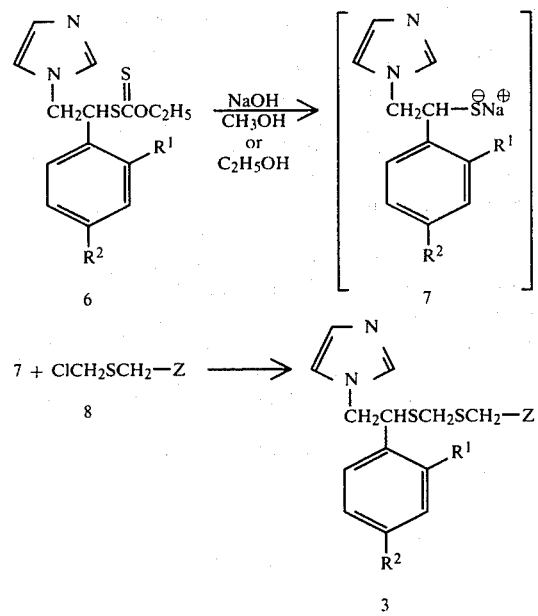

The starting xanthates 6 and their acid addition salts are known compounds and are readily prepared and hydrolyzed to afford the thiol salts 7 by the procedures disclosed in U.S. Pat. Nos. 4,038,409 and 4,039,677. The hydrolysis of the xanthate 6 or an acid addition salt of the xanthate 6 and the subsequent alkylation of the thiol salt 7 are usually conducted under an atmosphere of nitrogen to minimize oxidation. To the resulting alcoholic solution of the thiol salt 7 is added an approximately equimolar amount of the appropriately substituted chloromethyl arylmethyl sulfide 8 (Z=phenyl or thienyl). The reaction mixture is then stirred for periods of about 1–24 hours at temperatures of about 20°–80° C. Removal of the solvent leaves the crude product 3, which is usually a viscous oil. The oil can be purified by conversion to a solid acid addition salt, which is then recrystallized, or the oil can be purified by chromatographic techniques using silicic acid or alumina. If desired, the purified oils can then be converted to suitable acid addition salts by methods commonly employed in the art.

Although we prefer to use the xanthates 6 and the chloromethyl arylmethyl sulfides 8 (Z=phenyl or thienyl) in the instant syntheses, the subject compounds 3 can also be prepared according to the following general procedure:

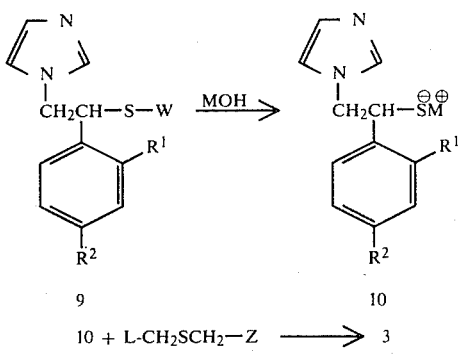

10 + L-CH₂SCH₂—Z ⟶ 3

11 wherein W is a group which when treated with an alkali metal hydroxide (M=sodium, lithium, potassium), in the presence of a suitable solvent, is cleaved by hydrolysis to afford the alkali metal thiolates 10. W, for example, can be one of the groups disclosed in U.S. Pat. Nos. 4,038,409 and 4,039,677, or can be a group such as, for example, amidino hydrochloride

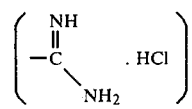

or N-methyl-2-pyridinium chloride

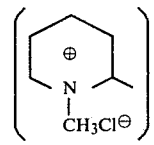

Treatment of the metal thiolate 10 with the alkylating species 11, wherein L is a conventional leaving group such as halo (preferably chloro) mesyloxy or tosyloxy, in the presence of a suitable inert solvent, affords the products 3. The starting compounds 9, wherein M=amidino hydrochloride or N-methyl 2-pyridinium chloride, can be prepared by contacting an imidazole of formula 12 in the presence of a suitable solvent with thiourea or N-methyl-2(1H)-pyridine thione, respectively.

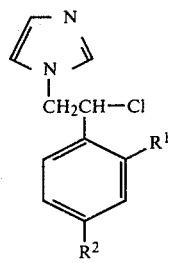

The 1-(β-chlorophenethyl)imidazoles 12 are known compounds and are described in U.S. Pat. No. 3,679,697. As depicted below, the subject compounds 3 can also be prepared by contacting an imidazole of formula 12 with a hemi-mercaptal of formula 13, in the presence of an inert solvent such as methanol, ethanol, N,N-dimethylformamide, benzene, toluene and the like, containing an acid binding agent such as sodium or potassium carbonate.

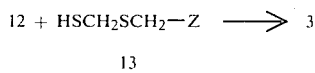

Alternatively, the alkali metal salt of 13 can be preformed with bases such as sodium ethoxide, sodium methoxide or an alkali metal hydride such as sodium hydride and the preformed salt of 13 contacted with 12, preferably in the same solvent in which it was formed, to yield the subject compounds 3. The hemi-mercaptals 13 are prepared by the procedure of H. Böhme, H. Fischer and R. Frank [*Ann. Chem.*, 563, 54, (1949)] which essentially consists of treating a chloromethyl sulfide, such as 8 with potassium sulfhydrate at low temperature.

Several of the chloromethyl arylmethyl sulfides 8 (Z=phenyl or thienyl) are described in the prior art. Those which are not previously described can be prepared by well-established techniques. For example, a mercaptan with the formula $HSCH_2-Z$, is treated with hydrogen chloride and formaldehyde to afford 8, or the procedure of Goralski and Burk [*J. Org. Chem.*, 42, 3094 (1977)] can be utilized, in which a mixture of the mercaptan, $HSCH_2-Z$, in bromochloromethane is stirred with powdered potassium hydroxide and a phase transfer catalyst to afford 8 after workup.

BIOLOGICAL METHODS AND RESULTS

A majority of the compounds of formula 3 were evaluated together with the prior art compound of formula 2 in a *Candida albicans* induced vaginal infection in mice and a *Trichophyton quinekeanum* induced skin infection in guinea pigs. Sabouraud broth was inoculated with *Candida albicans* and the inoculum incubated for two days at 28° C. on a rotary shaker. Groups of four to five female mice weighing between 18–21 grams were infected intravaginally with a 0.01 ml portion of the cell suspension containing $10^8$ cells/ml on day 0. The mice were treated subcutaneously with 0.5 mg of estradiol benzoate three days before and four days after infection. The test compounds were suspended in 1% carboxymethyl cellulose and 0.02 ml of the suspension was instilled intravaginally from day 0 (four hours after infection) to day 4 (5 applications). On day 7, vaginal exudate was taken by a thin glass rod and streaked on a YGP agar plate containing 100 mcg/ml of chloramphenicol. The plate was incubated for two days at 28° C. Viable cell count was made and graded by the following scores:

| Score | No. of Colonies |
| --- | --- |
| 4 | >3200 |
| 3 | 1001 ~ 3200 |
| 2 | 321 ~ 1000 |
| 1 | 101 ~ 320 |
| 0 | 0 ~ 100 |

A compound with a mean score of 1.5 or less was considered to be active (untreated control animals generally showed a score of >3).

In the guinea pig skin infection test, *Trichophyton quinekeanum* was cultured on a YGP agar slant at 28° C. for 10 days. Spores were collected from the mycelial mat and suspended in Sabouraud broth containing 2% of Tween 80. Groups of 3 male guinea pigs weighing between 400–500 g were used for each dose of test compound. The flanks of the animals were depilated and injured with sandpaper. The injured area was inoculated and rubbed with a glass rod on day 0 with 0.2 ml of the spore suspension containing $10^8$ CFU/ml. The test compound was combined with a 1:1 mixture of polyethylene glycol 400 and 4000, and 0.3 ml of the ointment was applied to the infected area on day 1, 3 and 5. Lesions were examined on day 7 and scored as follows: 0, normal; 1, erythema; 2, erythema with whitish area; 3, erythema and numerous whitish areas; 4, erythema with confluent scaling and whitish patches. A compound showing a mean score of 1.5 or less was considered active.

In the following Table I the antifungal activity of the test compound is reported as the $EC_{50}$ value, which is the percentage drug concentration giving 50% of the score of untreated control animals. The $EC_{50}$ was calculated by the method of least squares (K. Brounlee: Statistical Theory and Methodology in Science and Engineering, pages 345–349, Wiley Press, New York, 1965). In Table II a more detailed comparison on the in vivo antifungal activities of compound 3a and the isomeric prior art compound 2 are shown together with the data for compound 3b. Table III shows the in vitro antibacterial activity (in MIC's), of the compounds described in Table I, as against some gram-positive organisms.

| No. | A* | R¹ | R² | Z | EC50, Candida Vaginal Infection | EC50, Trichophyton Skin Infection |
| --- | --- | --- | --- | --- | --- | --- |
| 3a | C₄H₄O₄ | Cl | Cl | –⟨⟩–Cl | 0.0035 | 0.039 |
| 3b | HCl | Cl | Cl | –⟨⟩–Cl | 0.0011 | 0.053 |
| 3c | C₄H₄O₄ | Cl | Cl | –⟨⟩–CH₃ | 0.0042 | 0.046 |
| 3d | C₄H₄O₄ | Cl | Cl | Cl / –⟨⟩–Cl | 0.060 | 0.078 |
| 3e | HCl | Cl | Cl | Cl / –⟨⟩– / Cl | >0.3 | 0.085 |
| 3f | C₄H₄O₄ | H | Cl | –⟨⟩–Cl | N.T.* | N.T. |
| 3g | C₄H₄O₄ | H | Cl | Cl / –⟨⟩–Cl | N.T. | N.T. |

-continued

| No. | A* | R¹ | R² | Z | EC50, Candida Vaginal Infection | EC50, Trichophyton Skin Infection |
|---|---|---|---|---|---|---|
| 3h | C₂H₂O₄ | Cl | Cl | (5-chloro-2-thienyl) | 0.050 | 0.047 |
| 3i | HCl | Cl | Cl | (5-chloro-2-thienyl) | 0.0022 | 0.038 |
| 2 | C₄H₄O₄ | | | | >0.3 | 0.10 |

Structure 3: imidazole-CH₂CHSCH₂SCH₂—Z with R¹, R² substituted phenyl

Structure 2: imidazole·C₄H₄O₄, CH₂CHSCH₂CH₂S—(4-chlorophenyl), with 2,4-dichlorophenyl

*N.T. means not tested
*C₄H₄O₄ = fumaric acid  C₂H₂O₄ = oxalic acid.

TABLE II

In vivo antifungal activity of compounds 3a, 3b and 2

| | | Candida vaginal infection (N = 5) | | | | | | Trichophyton skin infection (N = 4) | | | | |
|---|---|---|---|---|---|---|---|---|---|---|---|---|
| Compound | Conc. (%) | Score | | | | | EC50 (%) (95% CL) (Confidence Limits) | Score | | | | (EC50 (%) (95% CL) |
| | | Determination A | B | C | D | Mean | | Determ. E | F | G | Mean | |
| Control | | 3.3 | 3.2 | 3.2 | 3.3 | | | 3.4 | 3.4 | 3.3 | | |
| 3a | 0.3 | — | — | — | — | — | 0.0035 | 1.0 | 0 | 0 | 0.33 | 0.039 |
| | 0.1 | — | — | — | — | — | (0.0020–0.0066) | 1.5 | 1.0 | 0.3 | 0.92 | (0.028–.05) |
| | 0.03 | 0.6 | 0.8 | 0 | 0.4 | 0.45 | | 1.8 | 2.5 | 1.5 | 1.9 | |
| | 0.01 | 1.5 | 0.4 | 1.3 | 1.3 | 1.1 | | — | — | 2.0 | 2.0 | |
| | 0.003 | 1.4 | 2.2 | 3.0 | 1.3 | 2.0 | | | | | | |
| | 0.001 | 3.0 | 2.2 | 2.8 | 2.0 | 2.5 | | | | | | |
| | 0.0003 | 2.8 | 2.2 | 3.4 | 2.5 | 2.6 | | | | | | |
| 2 | 0.3 | 3.4 | 1.8 | — | — | 2.6 | >0.3 | — | 0.5 | — | 0.5 | 0.10 |
| | 0.1 | 2.4 | 3.0 | — | — | 2.7 | | — | 2.3 | — | 2.3 | (0.047–0.22) |
| | 0.03 | 2.8 | 3.2 | — | — | 3.0 | | — | 2.3 | — | 2.3 | |
| 3b | 0.3 | 0 | 0 | — | — | 0 | 0.0011 | — | 0.3 | 0.3 | 0.3 | 0.053 |
| | 0.1 | 0.2 | 0 | — | — | 0.1 | (0.0001–0.0030) | — | 1.0 | 0.3 | 0.7 | (0.027–0.080) |
| | 0.03 | 0 | 0.8 | 2.4 | 0.8 | 1.0 | | — | 3.5 | 1.3 | 2.4 | |
| | 0.01 | 1.4 | 0.6 | 1.4 | 0 | 0.85 | | | | | | |
| | 0.003 | 0.4 | 2.0 | 2.2 | 0.2 | 1.2 | | | | | | |
| | 0.001 | 3.0 | — | 1.6 | 0.4 | 1.7 | | | | | | |
| | 0.0003 | — | — | 1.6 | 3.3 | 2.5 | | | | | | |

Treatment: 5 applications (day 0 to 4) against candida vaginal infection and 3 applications (day 1, 3 and 5) against trichophyton skin infection

TABLE III

| | MIC (μg/ml)[a] | | | | | |
|---|---|---|---|---|---|---|
| | Streptococcus | | | Staphylococcus aureus | | |
| Cpd No. | pneumoniae | pyogenes | faccalis | Strain A | Strain B | Strain C |
| 3a | 63 | 63 | >63 | 0.5 | >63 | >63 |
| 3b | >63 | >63 | >63 | >63 | >63 | >63 |
| 3c | 63 | 63 | 2 | 0.5 | >63 | 0.5 |
| 3d | 63 | 63 | >63 | 0.25 | >63 | 0.25 |
| 3e | >63 | >63 | 0.5 | 0.25 | >63 | 0.25 |
| 3f | 63 | 63 | 4 | 1 | >63 | 1 |
| 3g | 63 | 63 | 1 | 1 | 8 | 2 |
| 3h | 63 | 32 | 2 | 0.5 | 16 | 0.5 |
| 3i | 63 | 63 | 32 | 32 | 63 | 63 |
| 2 | 63 | >63 | 4 | 0.25 | 16 | 0.5 |

[a]S. pneumoniae and S. pyogenes were tested in 50% Nutrient Broth + 5% human serum, whereas S. faecalis and S. aureus were tested in Nutrient Broth.

EXPERIMENTAL SECTION

The following examples are only illustrative of certain preferred embodiments of the antimicrobial compounds of this invention, the structures of which as disclosed herein are supported by satisfactory infrared and proton magnetic resonance spectra. As employed herein and in the appended claims, all amounts and proportions are by weight unless otherwise indicated, temperatures are in °C., and melting and boiling points are uncorrected.

EXAMPLE 1

1-[2-(4-Chlorobenzylthiomethylthio)-2-(2,4-dichlorophenyl)ethyl]1-H-imidazole hydrogen fumarate (Table 1, Compound No. 3a)

To a stirred solution of sodium hydroxide (2.02 g, 0.05 mole) in ethanol (180 ml) at 25° under a blanket of nitrogen, was added 1-[2-(2,4-dichlorophenyl)-2-(ethoxythiocarbonylthio)ethyl]1-H-imidazole hydrogen oxalate* (4.51 g, 0.01 mole). After stirring at 25° for 0.75 hour a solution of 4-chlorobenzyl chloromethyl sulfide (2.07 g, 0.01 mole) in ethanol (2 ml) was added. The mixture was refluxed for twenty hours and concentrated to dryness. The residue was partitioned between diethyl ether and water. The ethereal layer was washed successively with H₂O, Na₂Co₃-H₂O, H₂O, brine and dried (Na₂SO₄). Removal of the ether left the free base (3.3 g) as a viscous brown oil. Treatment of a solution of the free base (3.3 g) in acetonitrile with fumaric acid (0.78 g) provided 2.5 g of the title compound, mp 120°–125°. Recrystallization from ethyl acetate gave colorless crystals, mp 121°–123°, of the analytical sample.

Anal. Calc'd for $C_{19}H_{17}Cl_3N_2S_2 \cdot C_4H_4O_4$: C, 49.34; H, 3.78; Cl, 19.00; N, 5.00; S, 11.45. Found: C, 49.70; H, 3.90; Cl, 18.94; N, 5.24; S, 11.39.

*U.S. Pat. Nos. 4,038,409 and 4,039,677

EXAMPLE 2

1-[2-(4-Chlorobenzylthiomethylthio)-2-(2,4-dichlorophenyl)ethyl]-1H-imidazole hydrochloride (Table I, Compound No. 3b)

Two grams of the hydrogen fumarate salt (3a), obtained as described in the preceding experiment, were partitioned between methylene chloride and aqueous potassium carbonate. The organic layer was washed with water and then dried over sodium sulfate. Removal of the solvent left the free base of the title compound as a viscous oil. Hydrogen chloride was bubbled into a solution of the free base in diethyl ether to afford colorless crystals of 3b, mp 115°–125°. Recrystallization from ethyl acetate afforded an analytical sample, mp 122°–125°.

Anal. Calc'd for $C_{19}H_{17}Cl_3N_2S_2 \cdot HCl$: C, 47.51; H, 3.78; Cl, 29.53; N, 5.83; S, 13.35. Found: C, 47.30; H, 3.78; Cl, 29.51; N, 6.02; S, 12.95.

EXAMPLE 3

1-[2-(4-Chlorobenzylthiomethylthio)-2-(4-chlorophenyl)ethyl]-1H-imidazole hydrogen fumarate (Table I Compound No. 3f).

To a stirred solution of sodium hydroxide (1.6 g, 0.04 mole) in ethanol (200 ml) at 25° under a blanket of nitrogen, was added 1-[2-(4-chlorophenyl)-2-(ethoxythiocarbonylthio)ethyl]-1H-imidazole hydrochloride* (3.63 g, 0.01 mole). After stirring at 25° for 0.75 hour, 4-chlorobenzyl chloromethyl sulfide (2.07 g, 0.01 mole) was added. The mixture was stirred under reflux for twenty hours and concentrated to dryness. The residue was partitioned between diethyl ether and water. The ethereal layer was washed successively with water and brine and then dried ($Na_2SO_4$). Removal of the ether left the free base (3.95 g) as a clear oil. Treatment of a solution of the free base (3.95) in acetonitrile with fumaric acid (1.1 g) provided 2.7 g of the title compound. mp 105°–110°. Recrystallization from acetonitrile afforded colorless crystals of the analytical sample, mp 104°–109°.

Anal. Calc'd for $C_{19}H_{18}Cl_2N_2S_2 \cdot C_4H_4O_4$: C, 52.57; H, 4.22; Cl, 13.49; N, 5.33; S, 12.20. Found: C, 52.56; H, 4.06; Cl, 13.71; N, 5.48; S, 11.73.

*U.S. Pat. NoS. 4,038,409 and 4,039,677

EXAMPLE 4

1-[2-(4-Chlorophenyl)-2-(2,4-dichlorobenzylthiomethylthio)ethyl]-1H-imidazole hydrogen fumarate (Table I, Compound No. 3g).

Repetition of the general procedure of Example 3, except that the 4-chlorobenzyl chloromethyl sulfide utilized therein was replaced by chloromethyl 2,4-dichlorobenzyl sulfide gave the title compound, mp 157.5°–160°.

Anal. Calc'd for $C_{19}H_{17}Cl_3N_2S_2 \cdot C_4H_4O_4$: C, 49.34; H, 3.78; Cl, 19.00; N, 5.00; S, 11.45. Found: C, 49.22; H, 3.99; Cl, 19.00; N, 5.12; S, 11.52.

EXAMPLE 5

1-[2-(5-Chloro-2-thienylmethylthiomethylthio)-2-(2,4-dichlorophenyl)ethyl]-1H-imidazole hydrochloride (Table I, Compound No. 3i)

To a stirred solution of sodium hydroxide (2.0 g, 0.05 mole) in ethanol (150 ml) at 25° under a blanket nitrogen, was added 1-[2-(2,4-dichlorophenyl)-2-ethoxythiocarbonylthio)ethyl]-1H-imidazole hydrogen oxalate (4.51 g, 0.01 mole). After stirring at 25° for 0.75 hour a solution of chloromethyl 5-chloro-2-thienylmethyl sulfide (2.13 g, 0.01 mole) in ethanol (4 ml) was added. The mixture was stirred for 2.5 hours at ambient temperatures and then was concentrated to dryness. The residue was partitioned between methylene chloride and dilute aqueous potassium carbonate. The $CH_2Cl_2$ was dried over $MgSO_4$ and concentrated to leave 4.5 g of the crude free base of the title compound as a viscous oil. The oil was chromatographed on silicic acid (50 g), eluting first with $CH_2Cl_2$ to remove the faster moving impurities and then with $CH_2Cl_2$-acetone (4:1) to afford 2.95 g of pure free base. A solution of the base in n-propanol was treated with 1.2 ml of 6 N hydrochloric acid. The resulting solution was concentrated and the residue crystallized from acetone to afford the title compound (2.26 g), mp 116°–118°.

Anal. Calc'd for $C_{17}H_{15}Cl_3N_2S_3 \cdot HCl$: C, 41.98; H, 3.32; Cl, 29.16; N, 5.76; S, 19.78. Found: C, 42.07; H, 3.28; Cl, 29.76; N, 5.90; S, 20.25

EXAMPLE 6

Repetition of the general procedure of Example 5 except that the chloromethyl 5-chloro-2-thienylmethyl sulfide utilized therein was replaced by:

(a) chloromethyl 2-chloro-3-thienylmethyl sulfide, (b) chloromethyl 2,6-dichlorobenzyl sulfide, (c) chloromethyl 4-methylbenzyl sulfide, and (d) chloromethyl 2,4-dichlorobenzyl sulfide, respectively, with the optional use of the indicated salt-forming acid, gave the following products, respectively:

(a) 1-[2-(2-Chloro-3-thienylmethylthiomethylthio)2-(2,4-dichlorophenyl)ethyl]-1H-imidazole hydrogen oxalate (Table I, Compound No. 3h), mp 107°–108°

Anal. Calc'd for $C_{17}H_{15}Cl_3N_2S_3 \cdot C_2H_2O_4$: C, 42.26; H, 3.17; Cl, 19.70; N, 5.19; S, 17.82. Found: C, 42.53; H, 3.15; Cl, 19.19; N, 5.40; S, 17.30

(b) 1-[2-(2,6-Dichlorobenzylthiomethylthio)-2-(2,4-dichlorophenyl)ethyl]1-H-imidazole hydrochloride (Table I, Compound No. 3e), mp 177°–180°

Anal. Calc'd for $C_{19}H_{16}Cl_4N_2S_2 \cdot HCl$: C, 44.33; H, 3.33; Cl, 34.44; N, 5.44; S, 12.46 Found: C, 44.11; H, 3.28; Cl, 34.37; N, 5.38; S, 12.45.

(c) 1-[2-(2,4-Dichlorophenyl)-2-(4-methylbenzylthiomethylthio)ethyl]-1H-imidazole hydrogen fumarate (Table I, Compound No. 3c), mp 123°–124°

Anal. Calc'd for $C_{20}H_{20}Cl_2N_2S_2 \cdot C_4H_4O_4$: C, 53.43; H, 4.48; Cl, 13.14; N, 5.19; S, 11.89. Found: C, 53.73; H, 4.46; Cl, 12.89; N, 5.17; S, 12.17.

(d) 1-[2-(2,4-Dichlorobenzylthiomethylthio)-2-(2,4-dichlorophenyl)ethyl]-1H-imidazole hydrogen fumarate (Table I, Compound No. 3d), mp 119°–121°

Anal. Calc'd for $C_{19}H_{16}Cl_4N_2S_2 \cdot C_4H_4O_4$: C, 46.48; H, 3.39; Cl, 23.86; N, 4.71; S, 10.79. Found: C, 46.68; H, 3.73; Cl, 23.60; N, 4.55; S, 10.82.

EXAMPLE 7

Chloromethyl Arylmethyl Sulfides (Compounds of Structure 8, Z=phenyl and thienyl)

Chloromethyl 5-chloro-2-thienylmethyl sulfide, chloro-methyl 2-chloro-3-thienylmethyl sulfide chloromethyl 2,4-dichlorobenzyl sulfide, chloromethyl 2,6-dichlorobenzyl sulfide, chloromethyl 4-methylbenzyl sulfide and 4-chlorobenzyl chloromethyl sulfide were synthesized according to the general procedure of Goralski and Burk [*J. Org. Chem.*, 42,3094 (1977)], which is exemplified for the preparation of chloromethyl 2,4-dichlorobenzyl sulfide, as follows. Benzyltriethylammonium bromide (350 mg) was added to a stirred mixture of 2,4-dichlorobenzyl mercaptan (7.12 g, 0.0387 mole) and powdered 85% potassium hydroxide (2.43 g, 0.0387 mole) in bromochloromethane (170 ml) at 25° and under a nitrogen atmosphere. Upon addition of the phase transfer catalyst an exothermic reaction started and the temperature rose to 35°. Stirring was continued for 1 hour at 45°–50° and the mixture concentrated to dryness on a rotary evaporator. The residue was partitioned between diethyl ether and cold water. The ethereal layer was washed successively with cold dilute aqueous sodium carbonate, $H_2O$ and brine and then dried over $Na_2SO_4$. Removal of the ether left the chloromethyl 2,4-dichlorobenzyl sulfide (8.17 g) as a mobile brown oil, which was pure enough for the alkylation step.

The 2-chloro-3-thienylmethyl mercaptan intermediate needed for the above synthesis was prepared as follows. A solution of 2-chloro-3-thienylmethyl bromide (5.36 g, 0.0254 mole) and thiourea (1.94 g, 0.0254 mole) in 95% ethanol (12 ml) was heated under reflux for 4 hours and concentrated to leave the crystalline isothiouronium salt. The salt was suspended in water (20 ml) containing sodium hydroxide (1.52 g, 0.038 mole) and the mixture warmed for 2 hours on a steam bath. The cooled mixture was acidified with 6 N HCl (7 ml) and extracted with diethyl ether. The ethereal extract was washed with water and dried ($Na_2SO_4$). Removal of the ether left 3.7 g of the mercaptan, a portion of which was distilled in a Kugelrohr apparatus to provide the analytical sample, bp 126°–128° (15 mm) as a colorless oil.

Anal. Calc'd for $C_5H_5ClS_2$: C, 36.46; H, 3.06; Cl, 21.53; S, 38.94. Found: C, 35.95; H, 3.04; Cl, 21.28; S, 38.73.

The antimicrobial compounds of this invention exhibit antifungal and antibacterial activity against a wide variety of human and animal pathogens and are accordingly useful not only in pharmaceutical applications but also in agricultural, industrial, household and other applications in which such activity is required. In general, antimicrobial compositions may contain such compounds in any concentrations, i.e. from about 0.1% to about 99.9% in a suitable or conventional carrier adapted for the intended use. For example, from about 10% to 90% concentrates may be supplied for dilution by the user to concentrations generally ranging from about 0.1% to 10%.

In pharmaceutical formulations compositions may be solid, semi-solid or liquid in form such as tablets, capsules, powders, suppositories, liquid solutions, suspensions, creams, lotions, gels, ointments and the like. Pharmaceutically acceptable non-toxic carriers, or excipients normally employed for solid formulations include tricalcium phosphate, calcium carbonate, kaolin, bentonite, talcum, gelatin, lactose, starch and the like; for semi-solid formulations there may be mentioned, for example, polyalkylene glycols, vaseline, petrolatum and other cream bases; for liquid formulations there may be mentioned, for example, water, oils of vegetable origin and low boiling solvents such as isopropanol, hydrogenated naphthalenes and the like. The pharmaceutical compositions containing the compounds of the present invention may be subjected to conventional pharmaceutical expedients such as sterilization and can contain conventional pharmaceutical excipients such as preservatives, stabilizing agents, emulsifying agents, salts for the adjustment of osmotic pressure and buffers. The compositions may also contain other therapeutically active materials.

The pharmaceutical compositions of this invention typically comprise a pharmaceutically acceptable, non-toxic carrier in combination with one or more compounds represented by formula 3 in an amount effective for relief or prevention of the specific condition being treated. Since the active compounds of this invention exhibit anti-fungal and anti-bacterial activity over a wide range of concentration, the effective amount may vary. For example, in topical formulations the amount may be about 0.1% to about 10% of the total pharmaceutical formulation while in other formulations the amount may be about 5 to 95% or more. Preferably the pharmaceutical compositions of this invention are formulated in unit dosage form to facilitate administration (unit dosage being the amount of active ingredients administered on one occasion).

In pharmaceutical applications, the subject compounds and compositions may be administered to humans and animals by conventional methods, e.g. topically orally, parenterally and the like. "Topical" administration includes intravaginal application while parenteral administration includes intramuscular as well as subcutaneous and intravenous injection. Intravenous injection of imidazole derivatives for certain systemic conditions has been demonstrated to be effective (see for example, Drugs 9, 419–420 (1975), which describes the intravenous administration of Miconazole, i.e. 1-[2,4-dichloro-$\beta$-(2',4'-dichlorobenzyloxy)phenethyl]imidazole nitrate, to patients with systemic candidiasis). Topical application is the preferred method of administration in pharmaceutical applications. For such treatment, an area having an existing fungal or bacterial growth, or to be protected against attack by fungi or bacteria, may be treated with the subject compounds of formula 3 or compositions containing them by, for example, dusting, sprinkling, spraying, rinsing, brushing, dipping, smearing, coating, impregnating and the like.

The exact regimen for pharmaceutical administration of the compounds and compositions disclosed herein will necessarily be dependent upon the needs of the individual subject being treated, the type of treatment, e.g., whether preventative or curative, the type of organism involved and, of course, the judgment of the attending practitioner. In general, for systemic (e.g., oral or parenteral) administration it is expedient to administer the active ingredient in amounts of between about 1 and 100 mg/kg body weight per day (preferably between about 5 and 50 mg/kg body weight per day) preferably distributed over several applications (e.g., in 3 individual doses) in order to achieve effective results. For localized (e.g., topical) administration, however, proportionately less of the active ingredient is required.

In agricultural applications, the subject compounds may be applied directly to plants (e.g., seeds, foliage) or to soil. For example, compounds of the present invention may be applied to seeds alone or in admixture with a powdered solid carrier. Typical powdered carriers are the various mineral silicates, e.g., mica, talc, pyrophyllite, and clays. The subject compounds may also be applied to the seeds in admixture with a conventional surface-active wetting agent with or without additional solid carrier. Surface-active wetting agents that can be used are any of the conventional anionic, non-ionic, amphoteric or cationic types. As a soil treatment for fungi and the like, the subject compounds can be applied as a dust in admixture with sand, soil or a powdered solid carrier such as mineral silicate with or without additional surface-active agent, or the subject compounds can be applied as an aqueous spray optionally containing a surface-active dispersing agent and a powdered solid carrier. As a foliage treatment, the subject compounds can be applied to growing plants as an aqueous spray which contains a surface-active dispersing agent with or without a powdered solid carrier and hydrocarbon solvents.

In industrial applications, the subject compounds may be used to control bacteria and fungi by contacting the pathogens with the compounds in any known manner. Materials capable of supporting bacteria and fungi may be protected by contacting, mixing or impregnating these materials with the subject compounds. In order to increase their effect, the subject compounds may be combined with other pesticidal control agents such as fungicides, bactericides, insecticides, miticides and the like. A particularly important industrial/agricultural use for the subject compounds of the present invention is as a food preservative against bacteria and fungi which cause deterioration and spoilage of foods.

This invention has been disclosed with respect to certain preferred embodiments, and it will be understood that modifications and variations thereof obvious to those skilled in the art are to be included within the spirit and perview of this application and the scope of the appended claims.

What is claimed is:

1. A compound of the formula 3:

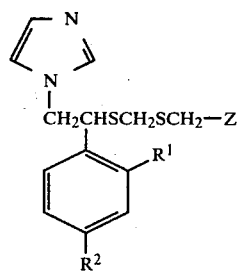

including the antimicrobial acid addition salts thereof, wherein;

$R^1$ and $R^2$ are independently hydrogen or halogen and Z is a mono or disubstituted phenyl moiety of the formula 4:

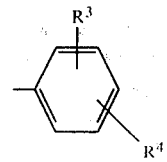

wherein $R^3$ and $R^4$ are independently hydrogen, halogen, (lower) alkyl or trifluoromethyl, with the proviso that $R^3$ and $R^4$ may not simultaneously both be trifluoromethyl.

2. The compound of claim 1 wherein the antimicrobial acid addition salt is the hydrochloride, hydrobromide, hydroiodide, nitrate, sulfate, phosphate, fumarate, oxalate, maleate, acetate, pyruvate, citrate, tartrate, methanesulfonate, ethansulfonate, p-toluenesulfonate, hydroxyethanesulfonate, sulfamate, malate, succinate, ascorbate, levulinate, propionate, glycolate, benzoate, mandelate, salicylate, lactate, p-aminosalicylate, 2-phenoxy benzoate, 2-acetoxy benzoate or 1,4-naphthalene disulfonate salt.

3. The dextrorotatory optical isomer of the compound of the formula 3 or antimicrobial acid addition salt thereof, as claimed in claim 1.

4. The levorotatory optical isomer of the compound of the formula 3 or antimicrobial acid addition salt thereof, as claimed in claim 1.

5. The compound of the formula 3 or antimicrobial acid addition salt thereof, as claimed in claim 1, wherein one of the $R^1$ or $R^2$ substituents is chloro and the other is chloro or hydrogen, and $R^3$ and $R^4$ are independently hydrogen, fluoro, chloro, (lower) alkyl or trifluoromethyl, with the proviso that $R^3$ and $R^4$ may not simultaneously both be trifluoromethyl.

6. The compound of the formula 3 or antimicrobial acid addition salt thereof, as claimed in claim 1, wherein one of the $R^1$ or $R^2$ substituents is chloro and the other is chloro or hydrogen and $R^3$ and $R^4$ are independently hydrogen, chloro or (lower) alkyl.

7. The compound of the formula 3 or antimicrobial acid addition salt thereof, as claimed in claim 1, wherein $R^2$ is chloro, $R^1$ is hydrogen or chloro and Z is 4-chlorophenyl or 2,4-dichlorophenyl.

8. The compound of the formula 3 or antimicrobial acid addition salt thereof, as claimed in claim 1, wherein $R^1$ and $R^2$ are chloro and Z is 4-chlorophenyl or 4-methylphenyl.

9. The compound of the formula 3 or antimicrobial acid addition salt thereof, as claimed in claim 1, wherein $R^1$ and $R^2$ are chloro and Z is 4-chlorophenyl.

10. The fumarate salt of the compound of claim 9.

11. The hydrochloride salt of the compound of claim 9.

12. The compound of the formula 3 or antimicrobial acid addition salt thereof, as claimed in claim 1 wherein $R^1$ and $R^2$ are chloro and Z is 4-methylphenyl.

13. The fumarate salt of the compound of claim 12.

14. The compound of the formula 3 or acid addition salt thereof, as claimed in claim 1, wherein $R^1$ and $R^2$ are chloro and Z is 2,4-dichlorophenyl.

15. The fumarate salt of the compound of claim 14.

16. The compound of the formula 3 or acid addition salt thereof, as claimed in claim 1, wherein $R^1$ and $R^2$ are chloro and Z is 2,6-dichlorophenyl.

17. The hydrochloride salt of the compound of claim 16.

18. The compound of the formula 3 or acid addition salt thereof, as claimed in claim 1, wherein R¹ is hydrogen, R² is chloro and Z is 4-chlorophenyl.

19. The fumarate salt of the compound of claim 18.

20. The compound of the formula 3 or acid addition salt thereof as claimed in claim 1, wherein R¹ is hydrogen, R² is chloro and Z is 2,4-dichlorophenyl.

21. The fumarate salt of the compound of claim 20.

22. A compound of the formula 3:

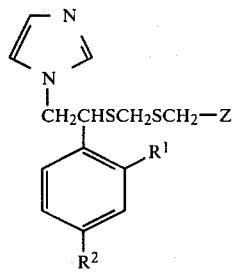
(3)

including the antimicrobial acid addition salts thereof, wherein;

R¹ and R² are independently hydrogen or halogen and Z is a 2 or 3 thienyl moiety of the formula 5:

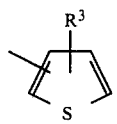
(5)

wherein R³ is hydrogen, halogen (lower) alkyl or trifluoromethyl.

23. The compound of claim 22 wherein the antimicrobial acid addition salt is the hydrochloride, hydrobromide, hydroiodide, nitrate, sulfate, phosphate, fumarate, oxalate, maleate, acetate, pyruvate, citrate, tartrate, methanesulfonate, ethansulfonate, p-toluenesulfonate, hydroxyethanesulfonate, sulfamate, malate, succinate, ascorbate, levulinate, propionate, glycolate, benzoate, mandelate, salicylate, lactate, p-aminosalicylate, 2-phenoxy benzoate, 2-acetoxy benzoate or 1,4-naphthalene disulfonate salt.

24. The dextrorotatory optical isomer of the compound of the formula 3 or antimicrobial acid addition salt thereof, as claimed in claim 22.

25. The levorotatory optical isomer of the compound of the formula 3 or antimicrobial acid addition salt thereof, as claimed in claim 22.

26. The compound of the formula 3 or antimicrobial acid addition salt thereof, as claimed in claim 22, wherein one of the R¹ or R² substituents is chloro and the other is chloro or hydrogen, and R³ is hydrogen, fluoro, chloro (lower) alkyl or trifluoromethyl.

27. The compound of the formula 3 or antimicrobial acid addition salt thereof, as claimed in claim 22, wherein one of the R¹ or R² substituents is chloro and the other is chloro or hydrogen and R³ is hydrogen, chloro or (lower) alkyl.

28. The compound of the formula 3 or antimicrobial acid addition salt thereof, as claimed in claim 22, wherein Z is the 3-thienyl moiety of formula 5 and R³ is chloro substituted at the 2-position.

29. The compound of the formula 3 or antimicrobial acid addition salt thereof, as claimed in claim 22, wherein Z is the 2-thienyl moiety of formula 5 and R³ is chloro substituted at the 5-position.

30. The compound of the formula 3 or acid addition salt thereof, as claimed in claim 22, wherein R¹ and R² are chloro and Z is 2-chloro-3-thienyl.

31. The oxalate salt of the compound of claim 30.

32. The compound of the formula 3 or acid addition salt thereof, as claimed in claim 22, wherein R¹ and R² are chloro and Z is 5-chloro-2-thienyl.

33. The hydrochloride salt of the compound of claim 32.

34. The composition useful for inhibiting the growth of fungi or bacteria comprising an antimicrobially effective amount of a compound or acid addition salt as defined in claim 1 in admixture with a suitable carrier.

35. A composition of claim 34 for pharmaceutical use wherein the carrier is a pharmaceutically acceptable carrier.

36. A composition of claim 35 for topical administration wherein the compound or acid addition salt is present in an amount ranging from about 0.1 to about 10 weight percent.

37. A method of inhibiting the growth of fungi or bacteria comprising applying to a host object containing, carrying or subject to attack by fungi or bacteria an antimicrobially effective amount of a compound or acid addition salt as defined in claim 1.

38. The method of claim 31 applied topically.

39. A composition useful for inhibiting the growth of fungi or bacteria comprising an antimicrobially effective amount of a compound or acid addition salt as defined in claim 22 in admixture with a suitable carrier.

40. A composition of claim 39 for pharmaceutical use wherein the carrier is a pharmaceutically acceptable carrier.

41. A composition of claim 40 for topical administration wherein the compound or acid addition salt is present in an amount ranging from about 0.1 to about 10 weight percent.

42. A method of inhibiting the growth of fungi or bacteria comprising applying to a host object containing, carrying or subject to attack by fungi or bacteria an antimicrobially effective amount of a compound or acid addition salt as defined in claim 22.

43. The method of claim 42 applied topically.

* * * * *